United States Patent [19]

Son et al.

[11] 4,251,435

[45] Feb. 17, 1981

[54] HIGH MOLECULAR WEIGHT PIPERIDINE DERIVATIVES AS UV STABILIZERS

[75] Inventors: Pyong-Nae Son, Akron; John T. Lai, Broadview Heights, both of Ohio

[73] Assignee: The B. F. Goodrich Company, Akron, Ohio

[21] Appl. No.: 99,166

[22] Filed: Nov. 30, 1979

[51] Int. Cl.$^3$ .................. C07D 471/10; C08K 5/35
[52] U.S. Cl. .................. 260/45.8 NE; 260/814; 546/17; 252/401; 252/403
[58] Field of Search .................. 546/17; 260/45.8 NP, 260/814; 252/401, 403

[56] References Cited

U.S. PATENT DOCUMENTS 3,979,513   9/1976   Galt et al. .................. 546/17

Primary Examiner—Henry R. Jiles
Assistant Examiner—Robert T. Bond
Attorney, Agent, or Firm—Nestor W. Shust

[57] ABSTRACT

Substituted high molecular weight hindered spiropiperidine compounds and polymer compositions stabilized by these compounds. The spiropiperidine compounds are prepared by reacting hindered 4-piperidinone hydrochloride with an activated benzene, such as resorcinol, in an acid medium.

16 Claims, No Drawings

HIGH MOLECULAR WEIGHT PIPERIDINE DERIVATIVES AS UV STABILIZERS

BACKGROUND OF THE INVENTION

Polymers have become one of the most vitally used materials in the production of innumerable products of manufacture. However, polymeric materials have an important deficiency, that is, they are subject to ultraviolet and oxidative degradation which affects their aesthetic appearance. Degradation exhibits itself as a partial or total loss of structural integrity, discoloration of the product, loss of flexibility, or a combination of the above phenomena.

To protect polymeric materials from the undesirable degradation, a variety of stabilizers can be added to them. The most often used stabilizers are antioxidants, antiozonants, heat stabilizers and ultraviolet (UV) light stabilizers. More often, to afford maximum protection against all types of degradations, a mixture of stabilizers, such as for example antioxidants, and UV light stabilizers, are usually employed.

A variety of UV light stabilizers are known in the prior art such as benzoates, benzotriazoles, benzophenones, and more recently, hindered amine or piperidine type compounds. A rather extensive list of different piperidine type UV light stabilizers are listed in U.S. Pat. No. 4,049,647. However, all of the prior art piperidine type UV light stabilizers are of relatively low molecular weight. The present invention deals with nonpolymeric but high molecular weight piperidine compounds which are useful as UV light stabilizers.

SUMMARY OF THE INVENTION

This invention is directed to a novel class of high molecular weight hindered piperidine compounds which are very effective in stabilizing a variety of polymers. More specifically, the present invention is directed to piperidine compounds having the structure

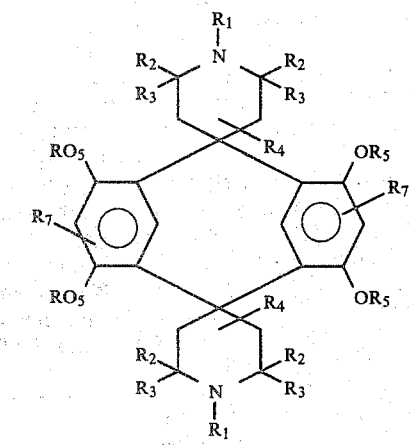

wherein $R_1$ is hydrogen, alkyl, oxyl group, alkoxy, alkenyl, alkynyl, aralkyl, alkaryl, hydroxyalkyl, haloalkyl, cyanoalkyl, amino or iminoalkyl, an ether group, hydroxyalkyl or cyanoalkyl ether group, or the group

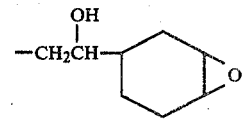

$R_2$ and $R_3$ each independently is alkyl, or $R_2$ and $R_3$, together with the ring carbon atom to which they are attached form cyclohexyl or cyclohexylalkyl group; $R_4$ each independently is alkyl or alkoxy group; $R_5$ each independently is hydrogen, alkyl, or the group $$-\underset{\underset{O}{\|}}{C}-R_6$$

where $R_6$ is alkyl, phenyl or alkaryl, and $R_7$ each independently is hydrogen or alkyl.

The above compounds of this invention can be prepared by reacting 2,2,6,6-tetraalkyl-4-piperidone hydrochloride with an activated benzene, such as resorcinol, in an acid medium.

DETAILED DESCRIPTION

The compounds of this invention may be represented by the formula

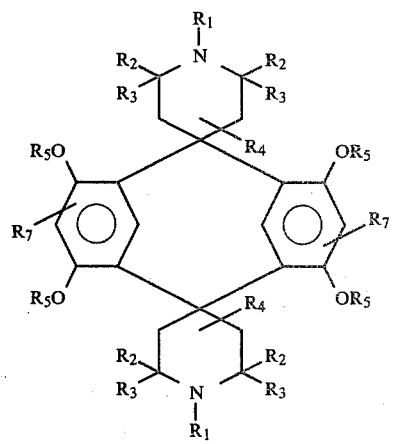

wherein each $R_1$ is independently hydrogen, alkyl or 1 to 18 carbons, oxyl group, alkoxy of 1 to 18 carbons, alkenyl of 2 to 6 carbons, alkynyl of 3 to 6 carbons, aryl, alkaryl or aralkyl of 7 to 14 carbons, hydroxyalkyl of 1 to 14 carbons, haloalkyl of 1 to 14 carbons, cyanoalkyl of 2 to 14 carbons, amino or iminoalkyl group of 2 to about 14 carbons, an ether group of 3 to 18 carbons total in the group, hydroxyalkyl or cyanoalkyl ether group of 4 to about 18 carbons total in the group, and the group

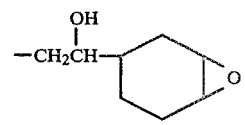

each $R_2$ and $R_3$ is independently alkyl group of 1 to about 12 carbons, or $R_2$ and $R_3$, together with the ring carbon atom to which they are bonded form cyclohexyl or alkyl substituted cyclohexyl group of 7 to about 14 atoms; each $R_4$ is independently hydrogen, alkyl or alkoxy group of 1 to 18 carbons; each $R_5$ is independently hydrogen, alkyl of 1 to 18 carbons or the group

where $R_6$ is alkyl of 1 to 18 carbons, phenyl or alkaryl of 7 to 14 carbons, each $R_7$ is independently hydrogen or alkyl of 1 to 18 carbons.

The group $R_1$ can be alkyl of 1 to 18 carbon atoms, preferably 1 to 12 carbon atoms and more preferably 1 to 4 carbon atoms. Illustrative examples of these groups are methyl, ethyl, n-propyl, iso-propyl, n-butyl, sec-butyl, t-butyl, n-hexyl, n-octyl, n-dodecyl, n-octadecyl and the like. The most preferred group is methyl. $R_1$ can also be oxyl group; alkoxy group having 1 to 18 carbons, preferably 1 to 12 and most preferably 1 to 4 carbon atoms such as methoxy, ethoxy, propoxy, butoxy, hexyloxy, octyloxy, and the like, the most preferred being methoxy group; alkenyl of 2 to 6 carbons such as allyl, α-methallyl, butenyl, hexenyl, acryloxy ethyl, methacryloxyethyl and methyl and the like; an alkynyl group such as propargyl; aralkyl such as benzyl, methyl and ethyl substituted benzyl and the like; aryl such as phenyl; alkaryl such as various isomers of 1 to 3 lower alkyl substituted phenyl where the alkyl groups have 1 to 4 carbon atoms such as methyl phenyl 2,3-,2,4-, 2,5- or 2,6-dimethyl phenyl and the like; o,p-diethyl benzyl and other lower alkyl substituents of benzyl; hydroxyalkyls such as 2-hydroxyethyl, 2-hydroxypropyl, 3-hydroxypropyl, 2-hydroxybutyl, 4-hydroxybutyl, 6-hydroxyhexyl, 8-hydroxyoctyl and the like; haloalkyls such as 2-chloroethyl, 2-bromoethyl, 2-fluoroethyl, 2-chlorobutyl, 4-chlorobutyl, 2-β-chloroethylhexyl and the like; cyanoalkyl such as 2-cyanoethyl, 3-cyanopropyl, 4-cyanobutyl, 8-cyanooctyl and the like; aminoalkyl such as 2-aminoethyl, 2-aminopropyl, 4-aminobutyl, 6-aminohexyl, α-methyl-2-aminoethyl; ethers such as methoxyethyl, ethoxyethyl, ethoxypropyl, octyloxyethyl, phenoxyethyl, p-methylphenoxypropyl, and the like; hydroxyalkyl ethers or cyanoalkyl ethers such as 2-hydroxyethyloxaethyl, p-(2-hydroxypropyl)-phenyloxapropyl, 4-hydroxybutyloxahexyl, 2-cyanoethyloxaethyl, 2-hydroxyethyldi(oxaethyl), and the like.

Groups $R_2$ and $R_3$ are preferably alkyl groups of 1 to 4 carbons and most preferably methyl. Illustrative examples of these groups are methyl, ethyl, n-propyl, iso-propyl, n-butyl, sec-butyl and tert-butyl. Groups $R_2$ and $R_3$, together with the ring carbon atom to which they are bonded can form cycloalkyl or lower alkyl substituted cyclohexyl such as methyl cyclohexyl, ethyl cyclohexyl, dimethyl cyclohexyl and the like.

Groups $R_4$ can be hydrogen or alkyl or alkoxy groups of 1 to 18 carbons such as methyl, ethyl, n-propyl, iso-propyl, n-butyl, n-hexyl, n-octyl, n-decyl, n-dodecyl, n-tetradecyl, n-octadecyl and the like as well as the corresponding alkoxy groups. Preferred are hydrogen, alkyl and alkoxy groups of 1 to 4 carbon atoms, especially methyl and methoxy groups.

Groups $R_5$ can be hydrogen or alkyl groups of 1 to 18 carbons such as those illustrated above, preferably those having 1 to 4 carbons; i.e., methyl, ethyl, n-propyl, iso-propyl, n-butyl, sec-butyl and tert-butyl. It can also be an aryl group such as phenyl or alkaryl of 7 to 14 carbons such as methyl phenyl, ethyl phenyl, various isomers of dimethyl and diethyl phenyl phenyl and the like, or a group of the formula

where $R_6$ is an alkyl of 1 to 18 carbons as illustrated above, preferably an alkyl of 1 to 4 carbons such as methyl, ethyl, isopropyl, n-propyl, n-butyl, sec-butyl or tert-butyl. $R_6$ can also be phenyl and, most importantly, alkyl substituted hydroxyphenyl where the alkyl groups have 1 to 8 carbon atoms, especially two-branched alkyl groups ortho to the hydroxyl group. Illustrative examples of such branched alkyl substituents are isopropyl, sec-butyl, tert-butyl, tert-octyl and the like. Alkyl substituents of 1 to 4 carbon atoms is preferred, especially methyl and tert-butyl groups. Additionally $R_6$ may be also alkaryl such as various isomers having 1 to 3 lower alkyl substituents on phenyl as, for example, methyl phenyl, 2,3-,2,4-,2,5-, or 2,6-dimethyl phenyl and the like.

The groups $R_7$ can be independently hydrogen, alkyl or alkoxy of 1 to 18 carbons, especially 1 to 4 carbons and preferably hydrogen or methyl. When $R_7$ is hydrogen it is understood that there are no substituents on the benzene rings other than the —$OR_5$ groups, in other words, $R_7$ would not appear as a substituent.

The dispiro tricyclic compounds of this invention can be prepared by reacting 2,2,6,6-tetraalkyl-4-piperidone hydrochloride with an activated benzene such as resorcinol or a m-dialkoxybenzene such as m-dimethoxybenzene. The reaction is carried out in an acid medium. The preparation of the instantly claimed compounds is described in greater detail in the examples.

High molecular weight piperidine compounds of the invention are very efficient and effectual UV stabilizers for materials that are subject to light degradation. These compounds are used in the substrates to be stabilized at a level of from about 0.05 part to about 10 parts by weight of compound per 100 parts by weight of the substrate. More preferably, they are employed at a concentration of from about 0.1 part to about 5 parts by weight per 100 parts by weight of the substrate material.

Materials that can be stabilized using the instant piperidines include any material that is subject to degradation on exposure to light, such as by discoloration and/or embrittlement. These materials can be low or high molecular weight materials, and particularly includes polymeric materials. Examples of materials that can be stabilized against degradation due to UV light are oils; monomers, particularly α,β-olefinically unsaturated monomer such as acrylates, dienes, vinyl nitriles, and the like; and other lower molecular weight materials such as alcohols, aldehydes, and the like. Examples of polymeric materials that can be stabilized are natural rubber, synthetic rubbers, such as cis-polyisoprene, styrene-butadiene rubber, diene-nitrile rubbers, polyepihalohydrin polymers and the like, polyurethanes, PVC resins, ABS resins, polystyrene, polyacrylonitrile, polymethacrylates, polycarbonates, varnish, phenol-formaldehyde resins, polyepoxides, polyesters, and polyolefin homo- and copolymers such as polyethylene, polypropylene, ethylene-propylene copolymers, ethylene-propylene-diene copolymers, ethylene-vinyl acetate copolymers, and the like. The piperidine compounds can also be used to stabilize mixtures and blends of polymeric materials such as ABS resin blends, PVC and polymethacrylate blends, and blends of polyolefin homopolymers and copolymers such as blends of polypropylene in EPDM polymers.

The compounds of this invention are particularly useful as UV stabilizers for polyolefin polymers such as the poly-α-monoolefin homopolymers and copolymers. The α-monoolefin monomers used to prepare the said polymers include ethylene, propylene, isobutylene, 1-butene, 1-pentene, 1-hexene, 4-methylpentene, and the like. Excellent results are obtained using said piperidines to stabilize polyethylene, ethylene-propylene copolymer and especially polypropylene.

Many known compounding ingredients may be used along with the piperidine compounds in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl organic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like; and other ingredients such as pigments, tackifiers, flame retardants, fungicides, and the like.

Compounding ingredients of particular interest to be used in the compositions of the invention are the antioxidant stabilizers and the phosphite co-stabilizers. As the piperidine compounds of the invention are particularly UV stabilizers, it is beneficial to add antioxidants to the compositions of the invention to achieve both UV light as well as oxidative and thermal stability. The antioxidants and co-stabilizers are used in the range of from about 0.01 part to about 10 parts by weight, preferably from about 0.05 part to about 5 parts by weight per 100 parts by weight of the material. Of the types of antioxidants to be used, the phenolic antioxidants are preferred.

Examples of phenolic antioxidants are 2,6-di-t-butylphenol; 2-methyl-1,4-dinonyl phenol; 1,1'-methylene-bis(2-naphthol); 4,4'-methylene-bis(2,6-di-t-butyl phenol); 4,4'-thiobis(6-t-butyl-m-cresol) 2,2'-methylene-bis-(4-ethyl-6-t-butyl phenol), 2,2'-thio-bis-(4-methyl-6-t-butyl phenol), 2,2'-methylene-bis-(6-t-butyl-4-ethyl phenol), 4,4'-butylidene-bis-(6-t-butyl-m-cresol), 2-(4'-hydroxy-3,5-di-t-butylanilino)-4,6-bis(octylthio)-1,3,5-triazine, hexahydro-1,3,5-tris-β-(3,5-di-t-butyl-4-hydroxyphenyl) propionyl-s-triazine, tris-(3,5-di-t-butyl-4-hydroxybenzyl) isocyanurate, as well as other antioxidants disclosed in U.S. Pat. No. 4,014,887, which disclosure is incorporated herein by reference. Although any phenolic antioxidant used in combination with a piperidine compound would improve the thermal and oxidative stability of the compositions, the more preferred phenolic antioxidants are those having alkylhydroxyphenyl substituents on an ester or a heterocyclic nucleus.

Examples of phenolic antioxidants having alkylhydroxyphenyl substituents on an ester nucleus are compounds of the formula

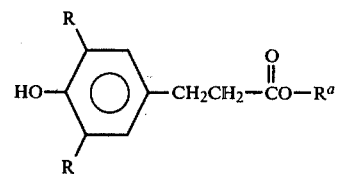

wherein R is hydrogen or an alkyl group of 1 to 9 carbon atoms, where at least one R must be an alkyl group, and $R^a$ is an alkyl group of 1 to 18 carbon atoms, exemplified by octadecyl 3-(3',5'-di-t-butyl-4'-hydroxyphenyl)propionate (see U.S. Pat. No. 3,330,859 for other examples); compounds of the formula

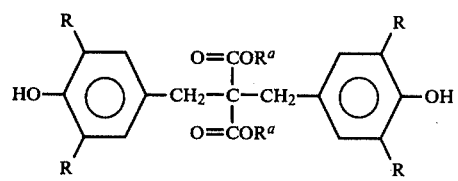

wherein R and $R^a$ are defined as above, exemplified by dilauryl α,α'-bis(3,5-di-t-butyl-4-hydroxybenzyl) malonate (see U.S. Pat. No. 3,627,725 for other examples); compounds of the formula

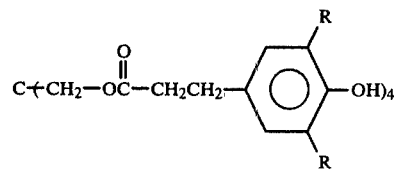

wherein R is defined as above, exemplified by tetrakis (methylene-3-(3',5'-di-t-butyl-4'-hydroxyphenyl) propionate) methane; and the like Examples of phenolic antioxidant compounds having alkylhydroxyphenyl substituents on a heterocyclic nucleus are compounds where the hetrocyclic nucleus is a triazine nucleus such as compounds of the formula

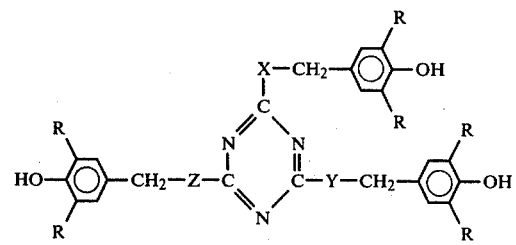

wherein X, Y, and Z are sulfur, oxygen, or nitrogen, and R is defined as above, exemplified by 2,2,4,6-tris(4-hydroxy-3,5-di-t-butyl benzlthio)-1,3,5-triazine (see British Pat. No. 977,589 for other examples); compounds of the formula

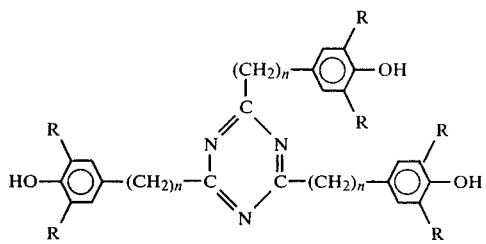

where R is defined as above, and n is 0 to 6, exemplified by 2,4,6-tris(3',5'-di-t-butyl-4'-hydroxybenzyl)-1,3,5-triazine (see U.S. Pat. No. 3,706,740 for other examples); compounds of the formula

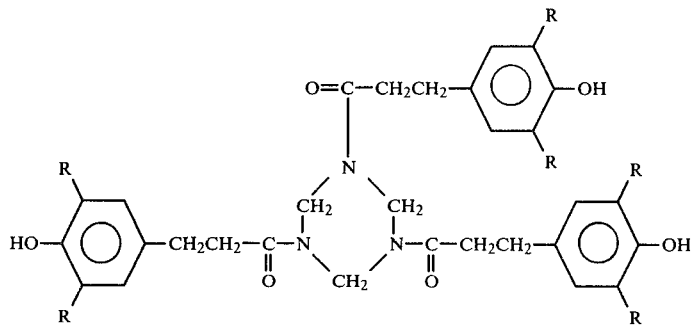

wherein R is defined as above, exemplified by hexahydro-1,3,5-tris-(β-(3,5-di-t-butyl-4-hydroxyphenyl) propionyl)-s-triazine (see U.S. Pat. No. 3,567,724 for other examples); compounds of the formula

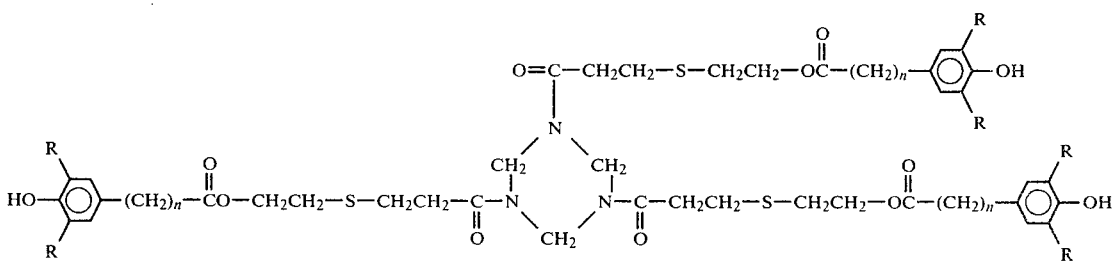

wherein R and n are defined as above, exemplified by 1,3,5-tris(4'-hydroxy-3',5'-di-t-butylphenylpropionyloxyethylthiopropionyl)hexahydro-1,3,5-triazine (see U.S. Pat. No. 3,694,440 for further examples); and the like.

Examples of phenolic antioxidant compounds having alkylhydroxyphenyl substituents on an isocyanurate nucleus are compounds of the formula

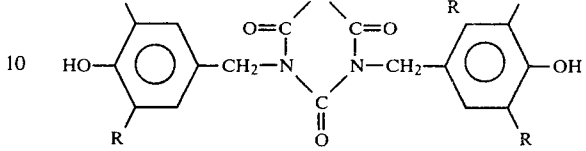

wherein R is defined as above, exemplified by tris(3,5-di-t-butyl-4-hydroxybenzyl)isocyanurate (see U.S. Pat. No. 3,531,483 for other examples); compounds of the formula

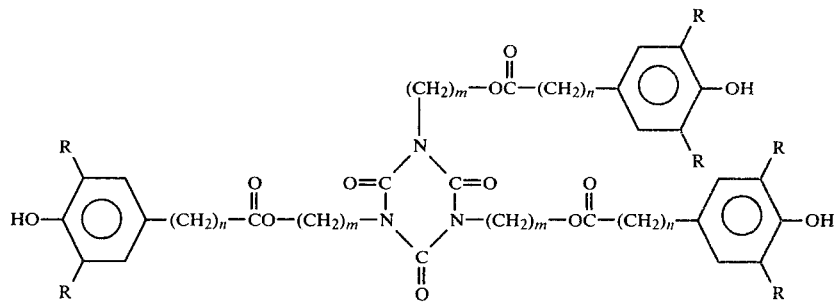

wherein R and n are defined as above, and m is 1 to 3, exemplified by 2,2',2''-tris(3-(3,5-di-t-butyl-4-hydroxyphenyl) propionyloxy) ethyl isocyanurate (see U.S. Pat. No. 3,678,047 for further examples), and the like.

The combination of a piperidine compound of this invention and a phenolic antioxidant compound has particular utility for stabilizing polyolefinic polymers against degradation caused by heat, air (oxygen), and UV light.

Also very useful in combination with piperidine compounds of this invention are organic phosphites which act as co-stabilizers. Illustrative examples of useful phosphites are, for example, triphenyl phosphite, diphenylalkyl phosphites, phenyldialkyl phosphites, tri(-nonylphenyl) phosphite, trilauryl phosphite, trioctadecyl phosphite, 3,9-isodecyloxy-2,4,8,10-tetraoxa-3,9-diphospha-[5.5]-undecane, tri-(4-hydroxy-3,5-di-tert, butylphenyl) phosphite, trinonyl phosphite, 3,9-octadecyloxy-2,4,8,10-tetraoxa-3,9-diphospha[5.5]-undecane, and the like.

It may also be advantageous to employ in combination with the compounds of this invention UV light absorbers such as benzophenes and benzotriazoles. The benzophenones have the general formula

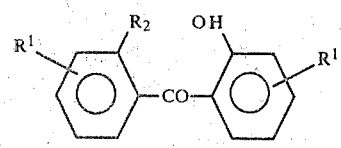

wherein $R^1$ is hydrogen, hydroxy group, halogen, lower alkyl group or alkoxy group having from 1 to 12 carbon atoms, and $R^2$ is hydrogen, hydroxy or alkyl from 1 to 12 carbon atoms.

In a preferred embodiment $R^1$ is hydrogen and $R^2$ is a straight chain alkyl group having from 8 to 12 carbon atoms. Illustrative examples of the above described benzophenones are listed below.

2-Hydroxy-4-methoxybenzophenone, 2,2'-Dihydroxy-4-methoxybenzophenone, 2-Hydroxy-4-methoxy-2'-carboxybenzophenone, 2,2-dihydroxy-4-n-octoxybenzophenone, 2-hydroxy-4-n-octoxybenzophenone, 5-chloro-2-hydroxybenzophenone, 2,4-dihydroxybenzophenone, 4-dodecycloxy-2-hydroxybenzophenone, 2-hydroxy-4-decyloxybenzophenone, 2,2'-dihydroxy-4,4'-dimethoxybenzophenone, 2,2'4,4'-tetrahydroxybenzophenone.

The benzotriazoles have the general formula

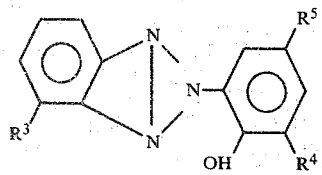

wherein $R^3$ is hydrogen, haolgen or lower alkyl, $R^4$ is hydrogen, chloride, lower alkyl, cycloalkyl or phenyl lower alkyl, $R^5$ is alkyl from 1 to 12 carbon atoms, cycloalkyl or phenyl lower alkyl, such that the sum of the atomic weights of the atoms contained in Groups $R^3$, $R^4$ and $R^5$ is at least 107.

In a more preferred embodiment, $R^3$ is hydrogen, chloride or methyl group; $R^4$ is hydrogen, chloride, t-butyl, t-amyl, cyclohexyl, benzyl or α-phenylethyl group; and $R^5$ is alkyl from 1 to 12 carbon atoms, cyclohexyl, benzyl or α-phenylethyl group. Illustrative examples of benzotriazoles employed in this invention listed below.

2(2'-hydroxy-5'-methylphenyl)-benzotriazole, 2-(2'-hydroxy-5'-methylphenyl)-benzotriazole-5-carboxylic acid butyl ester, 2-(2'-hydroxy-5'-tert-butylphenyl)-5-chlorobenzotriazole, 2-(2'-hydroxy-5'-amylphenyl)-benzotriazole, 2-(2'-hydroxy-5'-tert-butylphenyl)-benzotriazole, 2-(2'-hydroxy-3,5-dimethyl-phenyl)-5-methoxy-benzotriazole, 2-(2'-hydroxy-3',5'-dimethylphenyl)-5-methylbenzotriazole, 2-(2'-hydroxy-5'-methylphenyl)-benzotriazole, 2-(2'-hydroxy-5'-tert, butyl-phenyl-5-chlorobenzotriazole, 2,(2'-hydroxy-5'-amylphenyl) benzotriazole, 2-(2'-hydroxy-5'-tert-butylphenyl) benzotriazole, 2,(2'-hydroxy-5'-methoxyphenyl)-benzotriazole, 2-(2'-hydroxy-5'-methoxyphenyl)-benzotriazole, 2-(2'-hydroxy-5'-methylphenyl)-5,6-dichlorobenzotriazole, 2-(2'-hydroxy-5'-phenyl)-5-chlorobenzotriazole, 2-(2'-hydroxy-5'-cyclohexylphenyl)-5-chlorobenzotriazole, 2-(2'-hydroxy-5'-cyclohexyl-phenyl)-benzotriazole, 2-(2'-hydroxy-3',5'-dichlorophenyl)-benzotriazole, 2-(2'-hydroxy-4',5'-dichlorophenyl)-benzotriazole, 2-(2'-hydroxy-5'-phenyl)-benzotriazole, 2-(2'-hydroxy-5'-methoxy-phenyl-5-methylbenzotriazole.

Stabilization against thermal and oxidative degradation of polymeric substrates is further improved if a phenolic antioxidant is used in combination with a sulfur containing ester co-stabilizer (synergist) of the formula

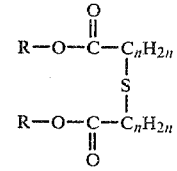

wherein R is an alkyl group having from 6 to 24 carbon atoms; and n is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

The compounds of the invention, and the other compounding ingredients if used, can be admixed with materials using known mixing techniques and equipment such as internal mixing kettles, a Banbury mixer, a Henschel mixer, a two-roll mill, an extruder mixer, or other standard equipment. Standard mixing times and temperatures can be employed. The objective is to obtain intimate and uniform mixing of the components. A favorable mixing procedure to use when adding a piperidine compound to a plastic material is to either dissolve or suspend the compound in a liquid such as hexane or benzene, add the plastic material in the form of a powder to the solution or suspension, evaporate off the liquid, and extruder mix the stabilized plastic material prior to forming the product.

The UV stability of a particular composition containing a polymeric material and a high molecular weight piperidine can be evaluated by exposing the prepared sample of the composition to Xenon or Carbon Arc light in a Weatherometer operating at a temperature, for example of about 140° F. (60° C.). Degradation of the sample can be followed by periodically measuring the degree of loss of tensile strength. The rapid formation of carbonyl indicates failure of the samples. This test procedure is well known, and is published in the text *Photodegradation, Photo-oxidation and Photostabilization of Polymers* by Ranby and Rabek, John Wiley and Sons, N.Y., N.Y., (1975) at page 120 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C.

The examples below are presented to further illustrate the invention. Exact procedures for the preparation of the high molecular weight piperidines of the compounds and polymeric materials, and exact test procedures and test results are disclosed.

EXAMPLE 1

2,2,2'',2''',6,6,6'',6'''-Octamethyldispiro [piperidine-4,2'-tricyclo[7.3.1.1$^{3,7}$]tetradeca-1'(13'),3',5',7'(14'),9',11'-hexaene-8',4''-piperidine]-4',6',10',12'-tetraol dihydrochloride (OPTT.2HCl)

In a 500 ml of three-neck flask were placed 57.4 g (0.52 mole) of resorcinol and 100 ml of methanol saturated with hydrogenchloride. The mixture was heated to 55°. A slurry of 2,2,6,6-tetramethyl-4-piperidone hydrochloride (100 g, 0.52 mole) in 100 ml of methanol saturated with hydrogenchloride was added portionwise to the above mixture. The addition took 8 minutes.

After reacting overnight at 56° C., the reaction mixture was cooled to room temperature and dumped into 400 ml of acetone. The resulting slurry was filtered and dried yielding 136.3 g. of white solid.

An analytical sample was prepared by washing 4.6 g of the crude product with hot chloroform twice. Then 1.7 g of the hot chloroform-insoluble solid was recrystallized from water and a trace of methanol to give 0.57 g of white solid, m.p. 305°–308° C. (dec.).

Anal. Calcd. for $C_{30}H_{44}N_2Cl_2O_4$: C, 63.48; H, 7.82; N, 4.93; Cl 12.49. Found: C,63.56; H, 8.01, N, 4.94; Cl, 12.63.

EXAMPLE 2

Preparation 2,2,2'',2''',6,6,6'',6'''-Octamethyldispiro[piperidine-4,2'-tricyclo[7.3.1.1$^{3,7}$]tetradeca-1'(13'),3',5',7'(14'),9',11'-hexaene-8',4''-piperidine]-4',6',10',12'-tetrayl Tetrakisacetate(OPTTA)

In a 500 ml three-neck flask were placed 11.3 g (0.02 mole) of OPTT.2HCl, 80 ml of pyridine, 8.2 g (0.08 mole) of acetic anhydride. The reaction mixture was heated to 50° C. and stirred for 12 hours. The reaction was worked-up by adding 300 ml of water to the reaction mixture and extracting twice with 150 ml of chloroform. The combined chloroform extract was washed with 200 ml of water, dried over anhydrous magnesium sulfate, filtered, and concentrated to leave a light yellow liquid. Removal of pyridine from the yellow liquid at 1.0 mm Hg left a yellow solid, which was washed with hexane to leave 2.3 g of hexane insoluble white solid.

The hexane filtrate was concentrated and washed with a minimum amount of ethanol to leave 0.9 g of white solid, mp 55°–7° C. A second crop (0.3 g) was obtained by concentrating the ethanol filtrate. The second crop has a mp of 54°–56° C.

Anal. Calcd for $C_{38}H_{50}N_2O_8$: C, 68.86; H, 7.60; N, 4.23; O, 19.31. Found: C, 68.56; H, 7.64; N, 4.10; O, 19.22.

EXAMPLE 3

Preparation of 2,2,2'',2''',6,6,6'',6'''-Octamethyldispiro[piperidine-4,2'-tricyclo[7.3.1.1$^{3,7}$]tetradeca-1'(13'),3',5',7'(14)',9',11'-hexaene-8',4''-piperidine]-4',6',10',12'-tetraol(OPTT)

The compound of Example 1 (OPTT.2HCl) is neutralized by adding thereto an equivalent amount of a base (sodium or potassium hydroxide, sodium or potassium bicarbonate, an amine such as pyridine and preferably triethylamine). The resulting product is the above named compound.

EXAMPLE 4

Preparation of 2,2,2'',2'''6,6,6'',6'''-Octamethyldispiro[piperidine-4,2'-tricyclo[7.3.1.1$^{3,7}$]tetradeca-1'(13'),3',5',7'(14'),9',11'-hexaene-8',4''-piperidine]-13',14'-dipentadecyl-4',6',10',12-tetraol(OPTDT)

The procedure of Example 1 is repeated except that 5-n-pentadecylresorcinol is used in place of resorcinol. The resulting product is then reacted exactly as described in Ex. 2 yielding the above named compound.

EXAMPLE 5

Preparation of 1,1''',2,2,2'''2''',6,6,6'',6'''-Decamethyl-dispiro[piperidine-4,2'-tricyclo[7.3.1.1$^{3,7}$]tetradeca-1'(13'),3',5',7'(14'),9',11'-hexaene-8',4''-piperidine]-4'6',10',12'-tetrayl tetrakisacetate(DPTTA)

The procedure of Example 1 is repeated except that 1,2,2,6,6-pentamethyl-4-piperidone hydrochloride is used in place of 2,2,6,6-tetramethyl-4-piperidone chloride. The resulting intermediate is then reacted exactly as described in Example 2 yielding the above named compound.

EXAMPLE 6

Preparation of 2,2,2'',2''',6,6,6'',6'''-Octamethyldispiro[piperidine-4,2'-tricyclo[7.3.1.1$^{3,7}$]tetradeca-1'(13'),3',5',7'(14'),9',11'-hexaene-8',4''-piperidine]-4',6'-diol-10',12'-diyl bis-[3,5-bis(1,1-dimethylethyl)-4-hydroxybenzoate]-(OPTDB)

In a 500 ml. flask were placed 21.45 g (0.37 mole) of OPTT.2HCl (prepared in Example 1), 285 ml. of N,N-dimethyl formamide and 30.0 g (0.11 mole) of 3,5-di-tert-butyl-4-hydroxybenzoyl chloride. The reaction was carried out according to the procedure described in Example 2. The resulting product was the above named compound which had a melting point with a wide range of 183°–200° C.

Anal. Calcd for $C_{60}H_{82}N_2O_8$: C, 75.12; H, 8.62; N, 2.92; O, 13.34. Found: C, 74.78; H, 8.70; N, 2.75; O, 13.60

EXAMPLE 7

2,2,2'',2''',6,6,6'',6'''-Octamethyldispiro[piperidine-4,2'-tricyclo[7.3.1.1$^{3,7}$]tetradeca-1'(13'),3',5'7'(14'),9',11'-hexaene-8',4''-piperidine]-4',6',10',12'-tetrayl Tetrakis[3,5-bis(1,1-dimethylethyl)-4-hydroxybenzoate](OPTTB)

In a 500 ml three-neck flask were placed 12.0 g (0.021 mole) of OPTT.2HCl, 250 ml of N,N-dimethylformamide, and 32.7 g (0.122 mole) of 3,5-di-tert-butyl-4- hydroxybenzoyl chloride. A steady stream of nitrogen was bubbled into the solution and heated with a stirring for 48 hours.

The pot temperature was maintained at 100°–110° C. Then the reaction mixture was cooled to room temperature and stirred for additional 48 hours. The resulting dark solution was neutralized by adding sodium hydroxide pellets and then poured into 1.8 liter of water. A gray taffy material was formed. It was isolated by decantation and washed with 200 ml. of water. Further washing with water and crushing resulted in a gray powder, which was air dried overnight to give 9.9 g of gray solid. Recrystallization from 2.5 ml of methylene chloride gave 5.3 g of off-white solid.

An analytical sample of a free amine was prepared by treating the above off-white solid with sodium hydroxide solution again and washing with water. Its melting point was 135°–141° C.

Anal. Calcd for $C_{90}H_{126}N_2O_{14}$ (as a dihydrate): C, 74.04; H, 8.70; N, 1.92; O, 15.34. Found: C, 73.90; H, 8.56; N, 1.84; O, 15.57.

EXAMPLE 8

Sample Preparation and Evaluation

Unstabilized polypropylene (Profax 6501 solid by Hercules, Inc.) in powder form was employed in tests. Over a period of 1.5 min. 48.0 g. of polypropylene were fed to a Brabender with the mixing head preheated to 190° C. Thereafter the desired amount of the antioxidant and the piperidine compound were added to polypropylene which was then mixed for three minutes at 30 RPM at 190° C. Mixed polypropylene was removed from the Brabender and pressed for a few minutes at room temperature to make a rough sheet. The sheet was chopped into small pieces and placed into a mold that was preheated to 215° C. and pressed for 3 minutes at 20,000 psi pressure after which the mold was cooled for 4 minutes. From the resulting sheet which was 20 mil thick dumbell samples were cut out. (The samples were one-half inch shorter on each end than the size specified in ASTM D638.).

Following the above-mentioned procedure for the Xenon Weatherometer test, polypropylene samples were tested to determine the time it would take for these samples to lose 50% of their tensile strength. All samples, including the one containing no UV stabilizer, contained 0.1 phr of 1,3,5-tris(3,5-di-tert-butyl-4-hydroxyhydrocinnamoyloxyethyl)hexahydro-s-triazine, a commercial antioxidant, needed to protect the samples from oxidative degradation. The antioxidant has no appreciable effect on UV stabilization. The UV stabilizers employed, and their concentration, is indicated in the table below.

| Sample | UV Stabilizer | Time to reach 50% Tensile Strength |
|---|---|---|
| A | None | 490 hours |
| B | 0.125 phr OPTTB | 850 |
| C | 0.25 phr OPTTB | 1160 |
| D | 0.50 phr OPTTB | 2000 |
| E | 0.125 phr OPTTA | 750 |
| F | 0.25 phr OPTTA | 750 |
| G | 0.25 phr OPTDB | 750 |
| H | 0.25 phr OPTDB | 1150 |

We claim:
1. A compound having the formula

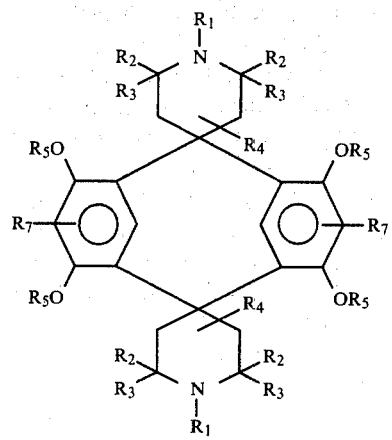

wherein each $R_1$ is independently hydrogen, alkyl of 1 to 18 carbons, oxyl group, alkoxy of 1 to 18 carbons, alkenyl of 2 to 6 carbons, alkynyl of 3 to 6 carbons, phenyl, alkaryl of 7 to 14 carbons and being selected from phenyl group substituted with 1 to 3 alkyl groups each having 1 to 4 carbon atoms, aralkyl or 7 to 14 carbons selected from benzyl and lower alkyl substituted benzyl, hydroxyalkyl of 1 to 14 carbons, haloalkyl of 1 to 14 carbons, cyanoalkyl of 2 to 14 carbons, amino or iminoalkyl group of 2 to about 14 carbons, an ether group of 3 to 18 carbons total in the group selected from ethers having alkyl group of 1 to 8 carbons, phenyl lower alkyl substituted phenyl, hydroxy or cyano-substituted alkyl of 4 to 18 carbons on phenyl substituted with hydroxy-lower alkyl, and the group

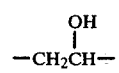

each $R_2$ and $R_3$ is independently alkyl group of 1 to about 12 carbons or $R_2$ and $R_3$, together with the ring carbon atom to which they are bonded form cyclohexyl or alkyl substituted cyclohexyl group of 7 to about 14 atoms; each $R_4$ is independently hydrogen, alkyl or alkoxy group each alkyl having 1 to 18 carbons; each $R_5$ is independently hydrogen, alkyl of 1 to 18 carbons or the group

where $R_6$ is alkyl of 1 to 18 carbons, phenyl, alkyl substituted hydroxyphenyl where said alkyl has 1 to 8 carbons or alkaryl of 7 to 14 carbons, and each $R_7$ is independently hydrogen or alkyl of 1 to 18 carbons.

2. A compound of claim 1 wherein $R_1$ is hydrogen, methyl, oxyl or methoxy; $R_2$ and $R_3$ are each methyl; $R_4$ is hydrogen; $R_5$ is hydrogen, methyl, acetyl or an alkyl substituted hydroxyphenyl where the alkyl groups have 1 to 4 carbon atoms; and $R_7$ is hydrogen.

3. A compound of claim 1 wherein $R_1$ is hydrogen or methyl, and $R_5$ is hydrogen, methyl, acetyl or a hydroxyphenyl having two tert-butyl groups ortho to the hydroxyl group.

4. A compound of claim 1 wherein $R_1$, $R_4$ and $R_7$ are each hydrogen, $R_2$ and $R_3$ are each methyl and $R_5$ are each acetyl.

5. A compound of claim 1 wherein $R_1$, $R_4$ and $R_7$ are each hydrogen, $R_2$ and $R_3$ are each methyl and two $R_5$ groups on one phenyl are hydrogen while the other $R_5$ groups are 3,5-di-tert-butyl-4-hydroxybenzyl groups.

6. A compound of claim 1 wherein $R_1$, $R_4$ and $R_7$ are each hydrogen, $R_2$ and $R_3$ are each methyl and each $R_5$ is 3,5-di-tert-butyl-4-hydroxybenzyl group.

7. A composition comprising a low or high molecular weight organic material subject to ultraviolet light degradation and from about 0.05 to about 10 parts by weight per 100 parts of said material of a high molecular weight piperidine of claim 1.

8. A composition of claim 7 wherein said material subject to ultraviolet light degradation is a polymeric material.

9. A composition of claim 8 wherein the polymeric material is a polyolefin homopolymer or copolymer.

10. A polyolefin homopolymer or copolymer composition stabilized against ultraviolet light degradation by incorporating therein 0.05 to 5 parts by weight of a compound of claim 2 per 100 parts of said polyolefin.

11. A polyolefin homopolymer or copolymer composition stabilized against ultraviolet light degradation by incorporating therein 0.05 to 5 parts by weight of a compound of claim 3 per 100 parts of said polyolefin.

12. A polypropylene composition stabilized against ultraviolet light degradation by incorporating therein 0.05 to 5 parts by weight of a compound of claim 3.

13. A composition of claim 7 containing additionally 0.01 to 10 parts by weight per 100 parts of said material of a phenolic antioxidant.

14. A composition of claim 9 containing additionally of 0.05 to 5 parts by weight per 100 parts of a polyolefin of a phenolic antioxidant.

15. A composition of claim 7 containing additionally 0.01 to 10 parts by weight per 100 parts of said material of a phosphite co-stabilizer.

16. A composition of claim 9 containing additionally 0.05 to 5 parts by weight per 100 parts of a polyolefin of a phosphite co-stabilizer.

* * * * *